(12) United States Patent
Su et al.

(10) Patent No.: US 9,671,558 B2
(45) Date of Patent: Jun. 6, 2017

(54) CHEMICALLY INDUCED OPTICAL SIGNALS AND DNA SEQUENCING

(75) Inventors: Xing Su, Cupertino, CA (US); Liming Wang, Santa Clara, CA (US); Jianquan Liu, Fremont, CA (US); Kai Wu, Mountain View, CA (US)

(73) Assignee: Intel Corporation, Santa Clara, CA (US)

( * ) Notice: Subject to any disclaimer, the term of this patent is extended or adjusted under 35 U.S.C. 154(b) by 1232 days.

(21) Appl. No.: 12/459,309

(22) Filed: Jun. 30, 2009

(65) Prior Publication Data

US 2010/0330553 A1 Dec. 30, 2010

(51) Int. Cl.
*C12Q 1/68* (2006.01)
*G02B 6/122* (2006.01)

(52) U.S. Cl.
CPC ......... *G02B 6/1221* (2013.01); *C12Q 1/6874* (2013.01)

(58) Field of Classification Search
None
See application file for complete search history.

(56) References Cited

U.S. PATENT DOCUMENTS

| | | | | |
|---|---|---|---|---|
| 5,620,850 | A * | 4/1997 | Bamdad | B82Y 15/00 422/69 |
| 6,846,638 | B2 * | 1/2005 | Shipwash | 435/7.1 |
| 7,302,146 | B2 * | 11/2007 | Turner | B01L 3/5085 356/38 |
| 7,389,029 | B2 * | 6/2008 | Rahman | B82Y 30/00 385/129 |
| 2004/0197793 | A1 * | 10/2004 | Hassibi et al. | 435/6 |
| 2006/0199193 | A1 | 9/2006 | Koo et al. | |
| 2009/0170716 | A1 | 7/2009 | Su et al. | |
| 2009/0208957 | A1 * | 8/2009 | Korlach et al. | 435/6 |

OTHER PUBLICATIONS

Czarnik et al. (Acc. Chem. Res. 1994, 27, p. 302-308).*
Iorio et al. (Bioorganic & Medicinal Chemistry Letters, 2001, vol. 11, p. 1635-1638).*
Kim et al. (Accounts of Chemical Research, 2009, vol. 42(1): p. 23-31).*
Levene et al. (Science, 2003, 299 (5607):682-686).*
Stora et al. (Langmuir, 2000, vol. 16, p. 5471-5478).*

(Continued)

*Primary Examiner* — Stephanie K Mummert
(74) *Attorney, Agent, or Firm* — Trop, Pruner & Hu, P.C.

(57) ABSTRACT

Methods for sequencing nucleic acids are presented. Sequencing is accomplished through the chemical amplification of the products of DNA synthesis and the detection of the chemically amplified products. In embodiments of the invention, a substrate is provided having a plurality of molecules of DNA to be sequenced attached and a plurality of molecules capable of chelating pyrophosphate ions attached, the DNA molecules to be sequenced are primed, and a next complementary nucleotide is incorporated and excised a plurality of times leading to the buildup of pyrophosphate ions locally around the DNA molecule to be sequenced. Pyrophosphate ions are captured by the substrate-attached chelators and optically detected to determine the identity of the next complementary nucleic acid in the DNA molecule to be sequenced.

20 Claims, 9 Drawing Sheets

(56) References Cited

OTHER PUBLICATIONS

Stephen S. W. Yeung, et al., "Electrochemical Real-Time Polymerase Chain Reaction," Journal of the Electrochemical Society, 2006, pp. 13374-13375, vol. 128, No. 41, S1-S2.

Jim Kling, "Ultrafast DNA Sequencing," Nature Biotechnology, 2003, pp. 1425-1427, vol. 21. No. 12.

M. Gabig-Ciminska, et al., "Electric Chips for Rapid Detection and Quantification of Nucleic Acids," Biosensors and Bioelectronics, 2004, pp. 537-546, vol. 19.

Guangxia Gao, et al., "Conferring RNA Polymerase Activity to a DNA Polymerase: A Single Residue in Reverse Transcriptase Controls Substrate Selection," Proc. Natl. Acad. Sci., USA, Biochemistry, 1997, pp. 407-411, vol. 94.

Angela M. Delucia, et al., "An Error-prone Family Y DNA Polymerase (DinB Homolog from Sulfolobus Solfataricus) Uses a 'Steric gate' Residue for Discrimination Against Ribonucleotides," Nucleic Acids Research, 2003, pp. 4129-4137, vol. 31, No. 14.

U.S. Appl. No. 11/073,160, "Sensor Arrays and Nucleic Acid Sequencing Applications," filed Mar. 4, 2005.

U.S. Appl. No. 12/319,168, "Nucleic Acid Sequencing and Electronic Detection," filed Dec. 31, 2008.

B.B. Rosenblum, et al., "New Dye-Labeled Terminators for Improved DNA Sequencing Patterns," Nucleic Acids Research, 1997, pp. 4500-4504, vol. 25, No. 22.

Anthony G. Navarro, et al., "Silica Waveguide Design and Fabrication Using Integrated Optics: A Link to Optical VLSI Photonics Integration for Semiconductor Technology," 22nd Annual Microelectronic Engineering Conference, 2004, pp. 64-70.

Jingyue Ju, et al., "Fluorescence Energy Transfer Dye-Labeled Primers for DNA Sequencing and Analysis," Proc. Natl. Acad. Sci, USA, Biophysics, 1995, pp. 4347-4351, vol. 92.

Ulrike Lieberwirth, et al., "Multiplex Dye DNA Sequencing in Capillary Gel Electrophoresis by Diode Laser-Based Time-Resolved Fluorescence Detection," Analytical Chemistry, 1998, pp. 4771-4779, vol. 70, No. 22.

K.T. Samiee, et al., "Optical Properties of Zero Mode Waveguides," Photonic Applications in Biosensing and Imaging, Proc. of SPIE, 2005, pp. 59690W1-59690W6, vol. 5969.

M.J. Levene, et al., "Zero-Mode Waveguides for Single-Molecule Analysis at High Concentrations," Science, 2003, pp. 682-686, vol. 299.

K.T. Samiee, et al., "Zero Mode Waveguides for Single-Molecule Spectroscopy on Lipid Membranes," Biophysical Journal, 2006, pp. 3288-3299, vol. 90.

Sook Kyung Kim, et al., "Chemosensory for Pyrophosphate," Accounts of Chemical Research, 2009, pp. 23-31, vol. 42, No. 1.

Mostafa Ronaghi, et al., "DNA Sequencing: A Sequencing Method Based on Real-Time Pyrophosphate," Science, 1998, pp. 363-365, vol. 281, No. 5373.

\* cited by examiner

CHEMICALLY INDUCED OPTICAL SIGNALS AND DNA SEQUENCING

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. application Ser. No. 11/073,160, entitled "Sensor Arrays and Nucleic Acid Sequencing Applications," filed Mar. 4, 2005, and is also related to U.S. patent application Ser. No. 12/319,168, entitled "Nucleic Acid Sequencing and Electronic Detection," filed Dec. 31, 2008, now pending, the disclosures of which are incorporated herein by reference.

BACKGROUND OF THE INVENTION

Field of the Invention

The embodiments of the present invention relate generally to methods and devices for nucleic acid sequencing and the optical detection of the products of nucleic acid sequencing reactions.

Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or suceptibility to many common diseases, such as cancer, cystic fibrosis, and sickle cell anemia. Determination of the entire three billion nucleotide sequence of the human genome has provided a foundation for identifying the genetic basis of such diseases. A determination of the sequence of the human genome required years to accomplish. Sequencing the genomes of individuals provides an opportunity to personalize medical treatments. The need for nucleic acid sequence information also exists in research, environmental protection, food safety, biodefense, and clinical applications, such as for example, pathogen detection (the detection of the presence or absence of pathogens or their genetic variants).

Thus, because DNA sequencing is an important technology for applications in bioscience, such as, for example, the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust methods for sequencing short lengths of nucleic acids (such as, for example, those containing 1-20 bases). Sequencing methods that provide increased accuracy and or robustness, decreased need for analysis sample, and or high throughput are valuable analytical and biomedical tools.

DETAILED DESCRIPTION OF THE INVENTION

Figure 1:
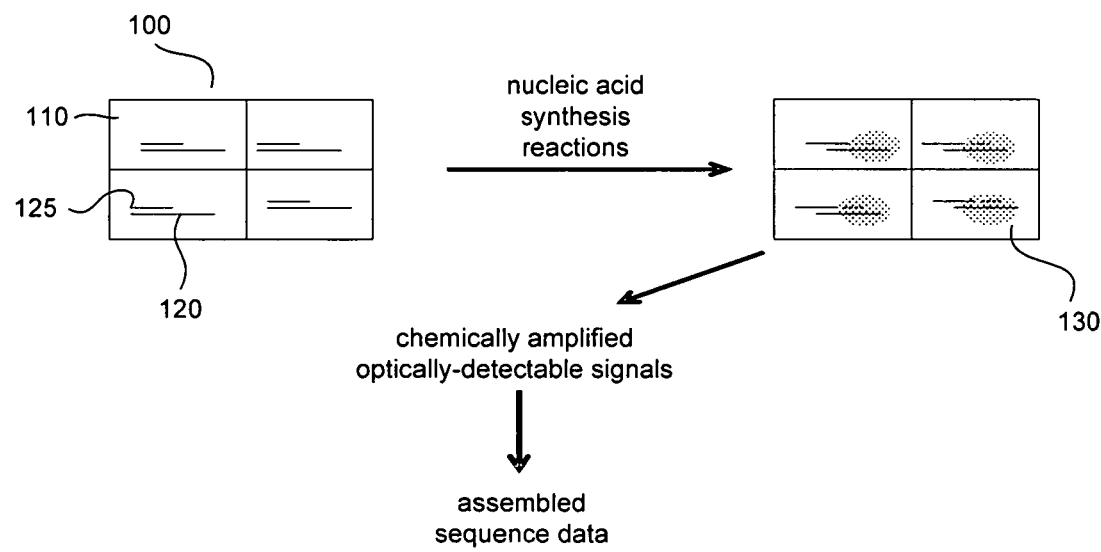
FIG. 1 provides a simplified diagram of a method for the parallel sequencing of nucleic acids employing chemical signal amplification and optical detection of chemically amplified sequencing reactions.

Embodiments of the present invention provide devices and methods for sequencing and detecting nucleic acids. Methods are provided according to embodiments of the invention by which whole genomes of organisms can be sequenced. In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). Additionally, non-naturally occurring nucleic acids that are susceptible to enzymatic synthesis and degradation may be used in embodiments of the present invention.

Methods for preparing and isolating various forms of nucleic acids are known. See for example, Berger and Kimmel, eds., *Guide to Molecular Cloning Techniques*, Methods in Enzymology, Academic Press, New York, N.Y. (1987); Sambrook, Fritsch and Maniatis, eds., *Molecular Cloning: A Laboratory Manual, 2nd Ed.*, Cold Spring Harbor Press, Cold Spring Harbor, N.Y. (1989); and Ausbel, F. M., et al., eds., *Current Protocols in Molecular Biology*, Wiley and Sons, Inc. (2007). Samples comprising RNA can be converted to DNA for sequencing using a reverse transcriptase enzyme to synthesize a complementary strand of DNA from the RNA molecule. Commercial kits for preparing nucleic acids are available, such as, for example, the SuperScript™ Double-Stranded cDNA Synthesis Kit from Invitrogen.

Methods are provided for sequencing nucleic acids in which amplification of the nucleic acid sample (i.e., increasing the number of copies of the nucleic acid molecules in the sample) optionally does not have to occur. As much as one third of the error during the sequencing of a nucleic acid sample has been reported to be due to errors introduced during the amplification of the nucleic acid sample. By not amplifying the sample to be sequenced, amplification-related errors can be avoided. Additionally, avoiding amplifying a sample avoids the concentration bias that can develop when a sample is amplified. The concentration bias that occurs during amplification is a result of the selective amplification advantage found for certain sequence populations, such that some sequences are amplified preferentially to a greater extent than other sequences. Because amplification-related errors are reduced, the methods of the present invention are useful for surveying for rare mutations among samples having a variety of components (mixed background components).

FIG. 1 provides a depiction of a generalized sequencing strategy according to embodiments of the invention. In FIG. 1, an array of detection regions 100, such as, for example, a zero-mode optical waveguide device, having reaction regions 110 and immobilized DNA molecules 120 is shown. One DNA molecule to be sequenced is immobilized per detection region 110 in this example. Before sequencing a sample of DNA, overlapped DNA fragments are immobilized randomly on the surface of a substrate so that statistically one DNA molecule 120 occupies the reaction region 110 of a detection region 100. A sample of DNA can be fragmented into smaller polymeric molecules using, for example, restriction enzymes or mechanical forces (shearing). The immobilized nucleic acid is primed with a primer 125 that is terminated with a nuclease resistant base and nucleic acid synthesis and deconstruction reactions are performed and amplified chemical products of the synthesis reactions 130 are created in the detection regions 110. The identified base position is then filled with a nuclease resistant base, and the reaction is repeated to determine a matching base for the next available position on the DNA strand to be sequenced. In this example, the amplified chemical products 130 are detected optically and sequence data for the immobilized DNA molecules is assembled. Reaction products in an array and their corresponding positions and optical signals are recorded and analyzed with a computer and software. Data from regions having no immobilized nucleic acid sample or a plurality of immobilized samples can be distinguished.

Figure 2:
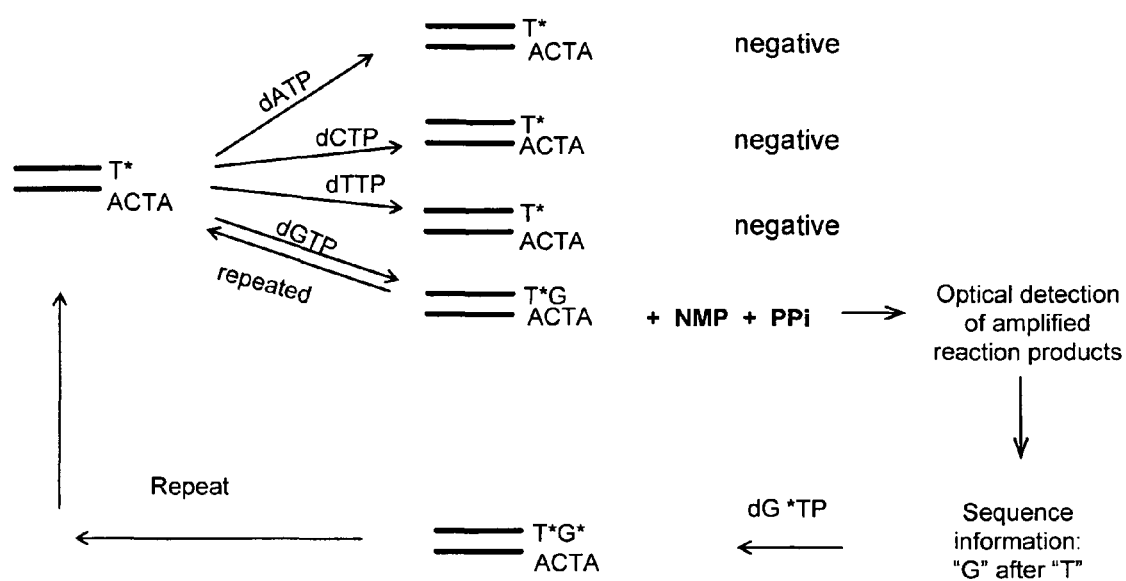
FIG. 2 shows an outline for a general nucleic acid sequencing strategy using the chemical amplification of reaction products and optical detection of amplified reaction products to assemble sequence information.

FIG. 2 provides an exemplary method for providing amplified chemical signals and sequencing data for nucleic acid sequencing reactions. In the method of FIG. 2, the chemical products resulting from the incorporation of a complementary dNTP (deoxynucleotide triphosphate) into a nucleic acid strand to be sequenced are amplified through the repeated addition and excision of the next complementary nucleotide. The DNA molecule to be sequenced is primed with a primer that is terminated with an exonuclease resistant nucleotide. In one embodiment, individual reactions are performed using one of four dNTPs and a determination is made regarding the next complementary nucleotide in the nucleic acid to be sequenced. In general, a test reaction comprises a polymerase, an exonuclease, and a deoxynucleoside triphosphatase (dATP (deoxyadenosine triphosphate), dCTP (deoxycytidine triphosphate), dGMP (deoxyguanosine triphosphate), or dTMP (deoxythymidine triphosphate), for example). A complementary nucleotide is incorporated into the primed growing DNA molecule that is terminated with a nuclease resistant base through the action of a polymerase enzyme. Typical useful polymerase enzymes include DNA polymerases, such as for example, *E. coli* DNA polymerase I and the commercially available 9 N and Therminator DNA polymerases (available from New England Biolabs, Inc., Beverly, Mass.). Thus, for example, where there is a cytosine on the strand to be sequenced, a guanine will be incorporated, where there is a thymidine, an adenosine will be incorporated, and vice versa. If the nucleoside triphosphate is incorporated into the growing strand in the test reaction, then a pyrophosphate ion (a "pyrophosphate," "PPi," or $P_2O_7^{-4}$) is released. In an amplification reaction, an exonuclease is used to remove the incorporated nucleoside monophosphate ($NMP^{-2}$), allowing another complementary nucleoside triphosphate to be incorporated and a second PPi to be released. Repetition of these addition and excision reactions provides amplification of reaction products. Thus, a positive test reaction (i.e., the detection of chemically amplified products) indicates that the base on the template DNA strand to be sequenced immediately after the priming base (the 3' base) of the primer strand is complementary to the test base (the one of four dNTPs that was used in the synthesis and deconstruction reaction). To sequence the next base on the template, the first identified base on the primer strand is filled or replaced with a nuclease-resistant nucleotide that then becomes the priming base for the test reaction. Nuclease-resistant nucleotides can be ribonucleotides or other modified nucleotides. A variety of polymerases are available that can incorporate ribonucleotides or modified nucleotides into DNA, such as for example, the commercially available Therminator DNA polymerase (available from New England Biolabs, Inc., Beverly, Mass.). See also, for example, DeLucia, A. M., Grindley, N. D. F., Joyce, C. M., *Nucleic Acids Research,* 31:14, 4129-4137 (2003); and Gao, G., Orlova, M., Georgiadis, M. M., Hendrickson, W. A., Goff, S. P., *Proceedings of the National Academy of Sciences,* 94, 407-411 (1997). Exemplary nuclease resistant bases include alpha-phosphorothioate nucleotides, and exemplary nucleases that cannot digest these resistant bases include exonuclease III. Reactions in which no product is detected indicate that the test reaction provided a nucleotide that was not complementary to the next base of the nucleic acid to be sequenced.

Figure 3A:
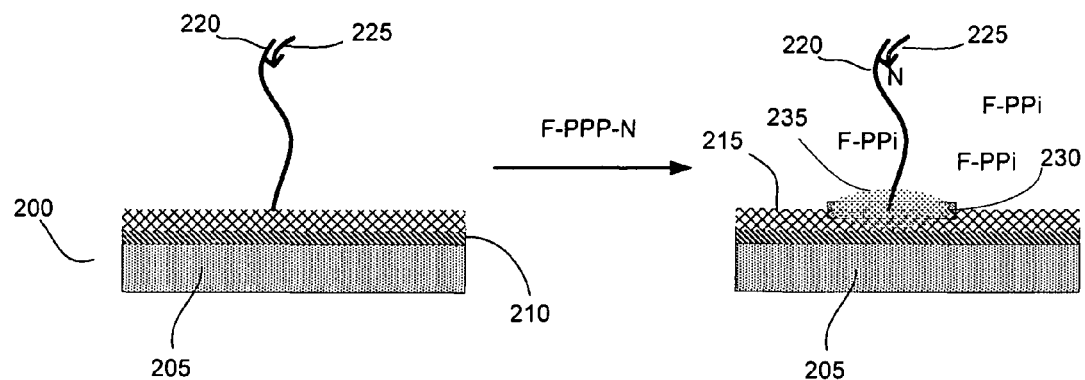
FIGS. 3A and 3B diagram how a chemically-amplified localized optical signal is generated during the sequencing reaction for a surface-attached nucleic acid.
Figure 3B:
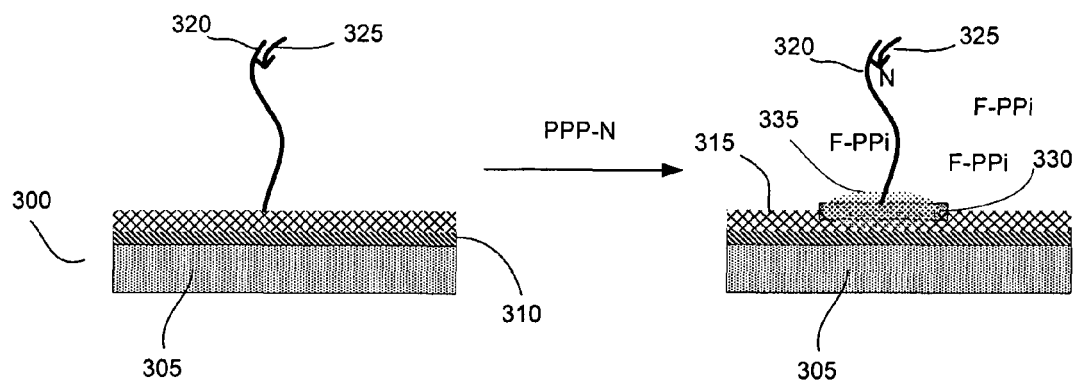

FIGS. 3A and 3B diagram a sequencing reaction for a nucleic acid molecule attached to a substrate. In FIG. 3A, a substrate 200 consists of a waveguide 205, a functional layer 210, a layer of attached pyrophosphate (PPi) chelator 215, and a molecule of DNA to be sequenced 220. The molecule of DNA to be sequenced 220 and the attached PPi chelator are attached to the functional layer 210 which facilitates light distribution or molecular attachment. In this example, the functional layer 210 is a lower index of refraction layer and can be considered to include any linker molecules, the nucleic acid molecules and chelating molecules, and liquid that may extend up to about 100 nm away from the waveguide core. The functional layer 210 has a refractive index that is less than the refractive index of the waveguide layer. Optionally, the surface of the substrate comprises a patterned metal layer (not shown) that facilitates other optical techniques through the creation of surface plasmons or zero mode optical waveguide phenomena. Typically, the optional patterned metal layer is a thin layer having a thickness of between 1 nm and 100 nm and is comprised of a metal such as for example, silver, gold or copper. The surface-attached molecule of DNA 220 is primed with a short hybridized complementary strand of DNA 225, also known as a priming molecule or primer. The primer molecule 225 is terminated with a nuclease resistant nucleotide. A solution is provided to the surface of the substrate 200, comprising one or more types of fluorescently labeled dNTPs (labeled F-PPP-N in FIG. 3A), a DNA polymerase enzyme, and an exonuclease. The fluorescently labeled dNTPs can be a single type of dNTP or a solution containing multiple dNTPs, such as fluorescently labeled dATP (deoxyadenosine triphosphate), dCTP (deoxycytidine triphosphate), dGMP (deoxyguanosine triphosphate), and dTMP (deoxythymidine triphosphate). For a solution of multiple types of dNTPs, each type of dNTP can be labeled with a different fluorescent label wherein the different fluorescent labels can be distinguished from each other spectroscopically. The incorporation and excision reactions of a next complementary nucleotide are allowed to proceed to create a build-up of reaction products including the fluorescently-labeled PPi molecules. Fluorescently labeled PPi molecules are captured by the surface-attached PPi chelator molecules 215. A region 230 around the surface-attached DNA molecule 220 develops in which PPi chelator molecules 215 have bound fluorescently-labeled PPi. Evanescently-generated fluorescent signals 235 can be detected using the waveguide to supply excitory radiation and a detector positioned above (not shown) the substrate 200 to receive and detect fluorescent radiation from the excited label. When the incorporation of a nucleotide has been detected or at the end of the test reaction, the substrate 200 is washed of the reactants, including the fluorescently-labeled PPi that is bound to the surface-attached chelators 215 and a next complementary nuclease-resistant nucleotide is incorporated into the priming strand 225, if the identity of the next complementary nucleotide is known. The above reactions are repeated for the next complementary nucleotide(s) to be determined and the sequence of the surface-attached DNA strand is assembled.

In FIG. 3B, a substrate 300 consists of a waveguide 305, a functional layer 310, and a layer of attached fluorogenic pyrophosphate (PPi) chelator 315, and a molecule of DNA to be sequenced 320. The molecule of DNA to be sequenced 320 and the attached PPi chelator are attached to the functional layer 310. The molecule of DNA to be sequenced 320 and the attached PPi chelator are attached to the functional layer 310 which facilitates light distribution or molecular attachment. The functional layer 310 has a refractive index that is less than the refractive index of the waveguide layer. In this example, the functional layer 310 is a lower index of refraction layer and can be considered to include any linker molecules, the nucleic acid molecules and chelating molecules, and liquid that may extend up to about 100 nm away from the waveguide core. Optionally, the surface of the substrate additionally comprises a patterned metal layer (not shown) that facilitates other optical waveguide techniques through the creation of surface plasmons or zero mode optical phenomena. Typically, the optional patterned metal layer is a thin layer having a thickness of between 1 nm and 100 nm and is comprised of a metal such as for example, silver, gold or copper. The surface-attached molecule of DNA 320 is primed with a short complementary strand of DNA 325. The primer molecule 325 is terminated with a nuclease resistant nucleotide. A solution is provided to the surface of the substrate 300, comprising dNTPs (labeled PPP-N in FIG. 3B), a DNA polymerase enzyme, and an exonuclease. The dNTPs can be a single type of dNTP or a solution containing multiple dNTPs, such as dATP (deoxyadenosine triphosphate), dCTP (deoxycytidine triphosphate), dGMP (deoxyguanosine triphosphate), and or dTMP (deoxythymidine triphosphate). The incorporation and excision reactions of a next complementary nucleotide are allowed to proceed to create a build-up of reaction products including a plurality of PPi molecules. The PPi molecules are captured by the surface-attached fluorogenic PPi chelator molecules 315. A region 330 around the surface-attached DNA molecule 320 develops in which PPi chelator molecules 315 have bound PPi. Evanescently-generated fluorescent signals 335 (for the cases in which evanescence is used to excite fluorescent labels) are detected using the waveguide to supply excitory radiation and a detector positioned above (not shown) the substrate 300 to receive and detect fluorescent radiation from the surface-attached fluorogenic chelator 315. In the alternative, when binding of PPi by the chelator releases a fluorescent dye, a region of no fluorescence indicates the production of reaction products and the incorporation of a complementary nucleotide. When the incorporation of a nucleotide has been detected or at the end of the test reaction, the substrate 300 is washed of the reactants, including the PPi that is bound to the surface-attached chelators 315 and a next complementary nuclease-resistant nucleotide is incorporated into the priming strand 325, if the identity of the next complementary nucleotide is known. The above reactions are repeated for the next complementary nucleotide(s) to be determined and the sequence of the surface-attached DNA strand is assembled.

Figure 4:
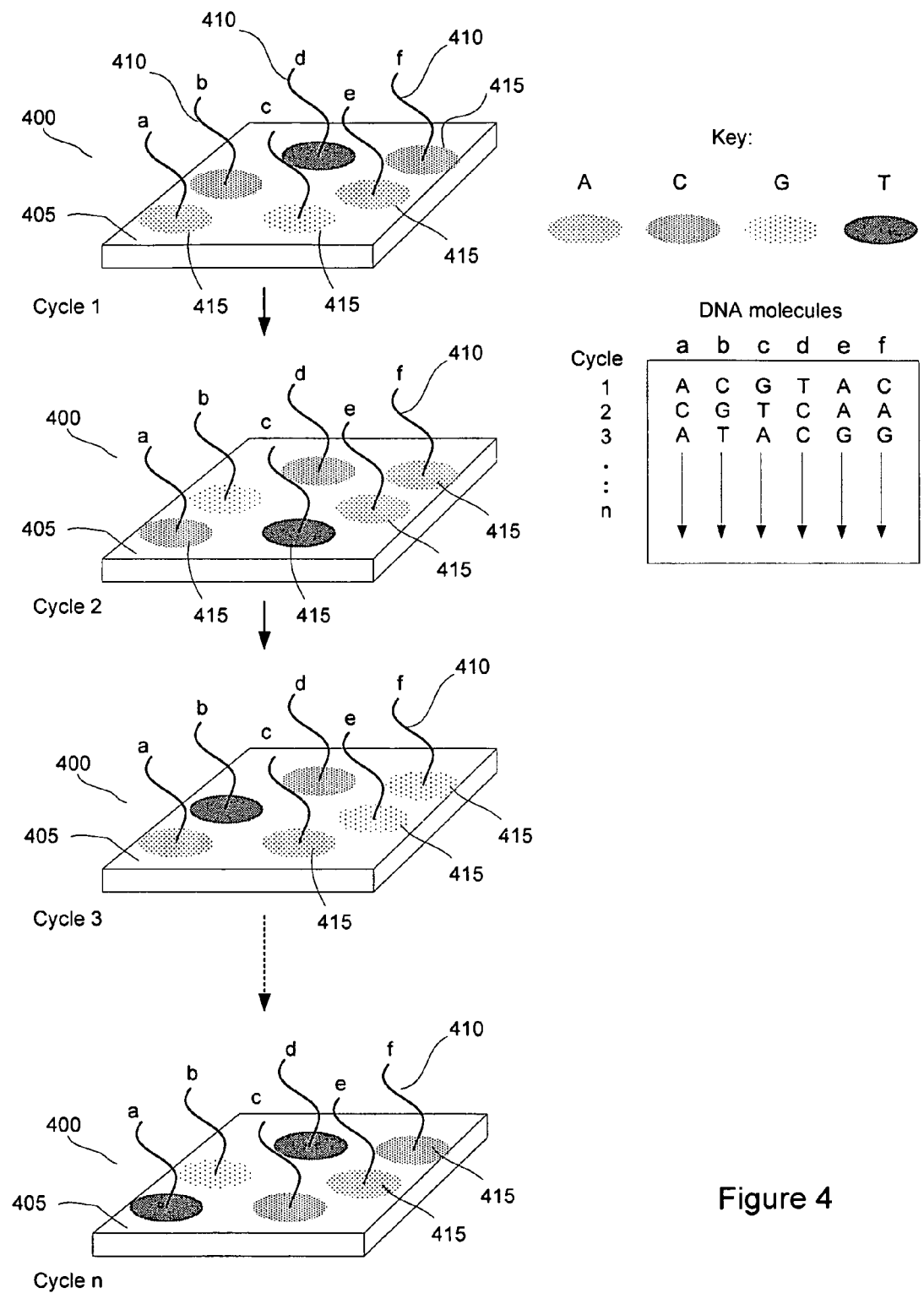
FIG. 4 diagrams multiplexed sequencing reaction for a plurality of DNA molecules.

FIG. 4 provides a diagram of parallel sequencing reactions for individual different DNA molecules. In FIG. 4, a substrate 400 comprises a waveguide 405 and individual DNA molecules 410 to be sequenced (labeled in FIG. 4 "a" through "f"). The DNA molecules 410 are attached to the surface of substrate 400. The substrate 400 surface additionally comprises surface-attached PPi chelating molecules (not shown). Sequencing reactions with chemical amplification of reaction products are performed on the surface-attached DNA molecules 410. The surface-attached DNA molecules 410 are primed (primer not shown) and terminated with a nuclease resistant nucleotide. A solution is provided to the surface of the substrate 400, comprising four types of fluorescently labeled dNTPs, a DNA polymerase enzyme, and an exonuclease. The fluorescently labeled dNTPs are fluorescently labeled dATP, dCTP, dGMP, and dTMP. In the example shown in FIG. 4, each type of nucleotide is labeled with a different distinguishable fluorescent label. The incorporation and excision reactions of a next complementary nucleotide are allowed to proceed to create a build-up of reaction products including a plurality of fluorescently-labeled PPi molecules. Fluorescently labeled PPi molecules are captured by the surface-attached PPi chelator molecules (not shown). A region around the surface-attached DNA molecule 410 develops in which PPi chelator molecules have bound fluorescently-labeled PPi molecules. Evanescently-generated fluorescent signals 415 can be detected using the waveguide to supply excitory radiation and a detector positioned above (not shown) the substrate 400 to receive and detect fluorescent radiation from the excited labels. The different distinguishable fluorescent labels are detected and distinguished (the labels fluoresce at different wavelengths) to determine the identity of the next complementary nucleotide. When the incorporation of a nucleotide has been detected or at the end of the test reaction, the substrate 400 is washed of the reactants, including the fluorescently-labeled PPi that is bound to the surface-attached chelators and a next complementary nuclease-resistant nucleotide is incorporated into the priming strand (not shown), if the identity of the next complementary nucleotide is known. The above reactions are repeated (labeled "Cycle 2-Cycle n" in FIG. 4) for the next complementary nucleotides to be determined and the sequence of the surface-attached DNA strand is assembled.

If a nucleoside triphosphate is incorporated into the growing strand in the test reaction, then a pyrophosphate (PPi) is released. The pyrophosphate can be degraded into two inorganic phosphates through ionic dissociation caused by water and catalyzed by pyrophosphatase. In an amplification reaction, an exonuclease is optionally used to remove the incorporated nucleoside monophosphates ($NMP^{-2}$), allowing another nucleoside triphosphate to be incorporated and a PPi to be released. Repetition of nucleotide incorporation and excision reactions provides chemical amplification of inorganic phosphate concentrations. Optionally, the nucleotide that is incorporated into the growing polymer is labeled and a buildup of labels is detected.

Nucleotides useful in the present invention include regular deoxyribonucleoside triphosphates (dNTP) and fluorescent dye-tagged dNTPs in which the fluorescent dye is attached to the gamma-phosphate of the dNTP (fluor-dNTP). The dNTP can also be fluorogenic, meaning that the intact fluor-dNTP is not fluorescent, but when the fluor-dNTP is hydrolyzed creating fluor-PPi or just fluor the dye's fluorescence becomes detectable. The phosphate groups on the fluor-PPi molecule are removable, for example, through the action of a phosphatase enzyme. The phosphatase enzyme optionally is included in the reaction solution comprising dNTPs, a DNA polymerase enzyme, and an exonuclease. In the situations in which phosphatase and or pyrophosphatase are used, detection of reaction products occurs in solution. In this case, metal nanogaps are a suitable structure for the signal generation and detection because the gaps can confine the signals to local areas within given periods of time. Pyrophosphate (PPi) or fluor-PPi is the byproduct of DNA polymerase reactions that incorporate complementary nucleotides into hybridized growing DNA molecules and PPi or fluor-PPi can be specifically captured by a chelating molecule. Nuclease resistant nucleotides include, for example, alpha-thiotriphosphate, alpha-methyltriphosphate, and alpha-boranophosphate nucleotides.

Figure 5:
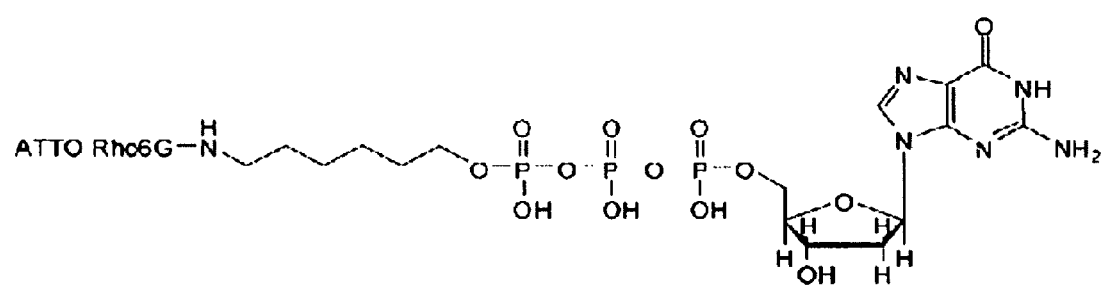
FIG. 5 provides an exemplary fluorescently labeled deoxynucleotide triphosphate (dNTP).

FIG. 5 provides the structure of an exemplary fluorescently-labeled nucleotide. In this example, the gamma phosphate of a dGTP has been labeled with ATTO Rho6G (rhodamine 6G). The labeled nucleotide ATTO Rho6G-dGTP can be incorporated into a growing DNA strand using, for example, 9 N and therminator DNA polymerases. Additional examples of fluorescent labels that can be attached to the gamma phosphate of a dNTP include, for example, cyanine dyes such as Cy3 and Cy5, rhodamine derivatives MR200-1 and JA169, oxazine derivative JA242 (see Lieberwirth, U. et al., *Multiplex Dye DNA Sequencing in Capillary Gel Electrophoresis by Diode Laser-based Timereolved Fluorescence Detection, Anal. Chem.*, 70:4771-4779 (1998) and Rosenblum, B. B., et al., *New Dye-labeled Terminators for Improved DNA Sequencing Patterns, Nucleic Acids Research,* 25:4500-4504 (1997)), and fluorescein derivatives (see Ju, J., et al., *Fluorescence Energy Transfer Dye-labeled Primers for DNA Sequencing and Analysis, Proc. Natl. Acad. Sci, USA,* 92:4347-4351 (1995)). In general, a large number of fluorescent dyes exist in the literature and are available for purchase from commercial sources. Further, nucleotides include nucleotide analogs and labeled nucleotide analogs, including methylated nucleotides, non-naturally occurring synthetic nucleotides, and or modified naturally occurring nucleotides.

Figure 6:
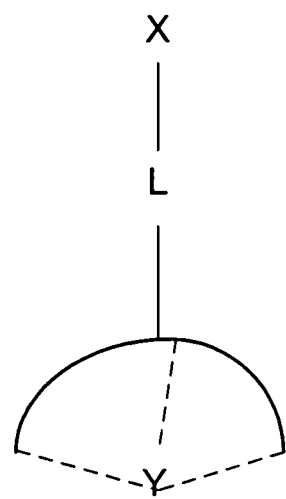
FIG. 6 shows an exemplary diagram of a pyrophosphate chelating molecule that can be attached to a surface.

In general, pyrophosphate chelators can be fluorescent after binding a PPi molecule or a fluorescent dye can be released when the chelator binds a PPi. In the case in which a fluorescent dye is released through the binding of a PPi molecule with a surface-attached chelating molecule, a region of no fluorescent emission during a sequencing reaction of a surface-attached DNA molecule indicates PPi production and the incorporation of a complementary nucleotide. An exemplary chelating molecule that can be attached to a surface is shown in FIG. 6. In FIG. 6, X represents an surface attachment site for the chelating molecule and can be a group such as, for example, a $-NH_2$ group, an $-OH$ group, a halogen, a thiol, a carboxyl group, an aldehyde, or an $-NH-NH_3$ group. The "L" in FIG. 6 represents a spacer with functional groups or a linker group and can be a group, such as for example, a polyethyle glycol (PEG), polyphosphate ($(PO_4)_n$), a structure such as $(-C-)_n$ which is from 1 to 100 atoms in length and can contain functional groups such as amine, hydroxyl, epoxy, aldehyde, carboxyl, and or thiol. The PPi chelating portion of the molecule (the ligand portion) is represented by the semicircle having an attached Y, in which Y is a dye or cofactor for the chelator such as metal ions, such as, for example, $Zn^{2+}$, $Cu^{2+}$, and or $Fe^{3+}$. See FIG. 9 for an exemplary chelator. A survey of molecules that are specific PPi chelators can be found in Kim, S. K., et al, "Chemosensors for Pyrophosphate," *Acc. Chem. Res.,* 42: 23 (2008).

Figure 7:
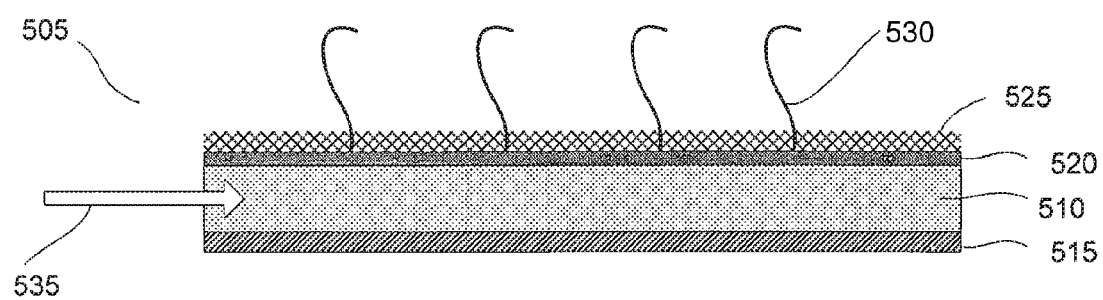
FIG. 7 provides an exemplary planar waveguide structure showing the direction of propagating light.

In general, the substrate is a planar waveguide (or slab waveguide), a zero mode optical waveguide device, or a plasmonic waveguide device. Planar waveguides typically have a rectangular geometry and consist of at least three layers of material having different dielectric constants. Light is confined to the middle layer by total internal reflection which occurs when the dielectric index of the middle layer is larger than that of the surrounding layers. In the planar waveguide, light is injected into the side of the waveguide as shown, for example, in FIG. 7. The critical angle for light injection depends on the index of refraction of the materials, which may vary depending on the wavelength of the light. Such propagation will result in a guided mode only at a discrete set of angles where the reflected planewave does not destructively interfere with itself. In the case of the planar waveguide, the substrate is constructed so that the molecular attachment area is evanescent and fluorescent dye molecules are excited only when they are in the proximity of the evanescent area. In this case, the functional layer is the organic structure between the waveguide layers and the DNA and chelator molecules (such as, for example, an organic linker or an organic linker and a silanation layer). It should have a refractive index that is lower than the middle waveguide material. Pyrophosphate or fluor-PPi produce detectable optical signals when the molecules are concentrated locally around the surface-attached DNA molecules during polymerase reactions. The reactions and optical signal recording are repeated in parallel for a set of immobilized DNA molecules and DNA sequence information is collected based on optical signal positions, timing, and wavelength of fluorescent emission. In general a waveguide is a physical structure that guides electromagnetic waves. Planar waveguides, for example, can be comprised of $SiO_2$, having surrounding layers with a different (lower) refractive index and can be formed, for example, from ion-exchange processes. See, for example, Haquin, H., et al., *Recent Developments in Ion-exchanged Fluoride Glass Planar Waveguides*, J. Non-Crystalline Solids, 236-7:460-463 (2003) and Navarro, A. G., *Silica Waveguide Design and Fabrication using Integrated Optics: A Link to Optical VLSI Photonics Integration for Semiconductor Technology*, $22^{nd}$ Annual Microelectronic Engineering Conference, 64-70 (May 2004). FIG. 7 provides an exemplary planar waveguide structure 505. In FIG. 7, a planar waveguide 510 is bounded on one side with a low refractive index material 515 and a low refractive index functional layer 520. Chelating molecules 525 and nucleic acids to be sequenced 530 are attached to the functional layer 520. An arrow 535 shows the direction of propagating light. Evanescence from the propagating light within the waveguide 510 is created in the region of the chelators 525. The evanescence is used to detect the chelation of reaction products from DNA sequencing reactions.

In general, zero mode optical waveguide devices are subwavelength optical nanostructures. To form a zero mode optical waveguide device, a transparent substrate or a substrate having a transparent surface layer is coated with a thin patterned metal layer forming the optical nanostructures. The optical nanostructures are sub-wavelength-sized holes in the metal layer. Two different resonance sizes can be used to design the structures: one is for excitation resonance and another is for emission resonance. Typically, the hole is round in shape and its diameter is less than one half of the wavelength of the light. the optional patterned metal layer is a thin layer having a thickness of between 1 nm and 100 nm and is comprised of a metal such as for example, silver, gold or copper. See, for example, Samiee, K. T., et al., *Zero Mode Waveguides for Single-molecule Spectroscopy on Lipid Membranes*, Biophys. J., 90:3288-3299 (2006) and Levene, M. J., et al., *Zero-mode Waveguides for Single-molecule Analysis at High Concentrations*, Science, 299:682-686 (2003). DNA to be sequenced is located within the hole through statistically random attachment schemes. In these embodiments, some holes will have one DNA to be sequenced immobilized, no DNA immobilized, or two or more nucleic acids to be sequenced immobilized. Holes having no nucleic acid or two or more nucleic acids immobilized are ignored. The transparent material is a material such as, for example, $SiO_2$, silicon nitride, or a glass or quartz layer.

Further, the substrate can be a plasmonic waveguide device. In a plasmonic waveguide device, a thin patterned metal layer confines and guides light. The light is emitted at the edges of the metal layer. The substrate on which the metal layer is patterned does not need to be transparent and a variety of materials are possible. For example, the substrate can be silicon, silicon dioxide, glass, or a polymer. In these plasmonic waveguide embodiments the thickness and type of metal layer are important to the operation of the device. Typically the metal layer has holes that have a linear or rectangular shape in which the longest dimension of the hole is optionally larger than the wavelength of light used to probe the DNA sequencing reaction. The nucleic acid to be sequenced can be attached either at the edge of the metal surrounding the hole or in the region of the waveguide surface having no metal. In one embodiment, the chelators and nucleic acid molecules to be sequenced are attached in the holes. One nucleic acid molecule to be sequenced is attached in one hole (attached so that statistically one nucleic acid molecule occupies one hole.) Metals that are useful include copper, silver, gold and aluminum, for example. Exemplary plasmonic waveguide devices include those described in the following reference: Jun, Y. C., et al., *Broadband Enhancement of Light Emission in Silicon Slot Waveguides*, Optics Express, 17:7479-7490 (2009).

Affinity agents (PPi chelators) and DNA molecules to be sequenced are co-immobilized on optical substrates (such as waveguides). For example, the waveguide surface is functionalized with one of or combination of amine, aldehyde, epxoy, thiol, groups, and DNA can be functionalized with amine (for surface bearing carboxy, epoxy, and or aldehyde functional groups) and carboxyl (for surface bearing amine groups), thiol (for surface of gold) Various conjugation chemistries are available to join the functional groups (for example, EDC for amine-carboxyl). The concentration of DNA molecules can be controlled in several ways: by limiting the density of surface functional groups or by limiting the quantity of DNA molecules to be attached. Typically, the longer the DNA molecules to be sequenced, the less density is needed. For example, a 300 nucleotide long DNA is about 100 nm, thus ideally there should be an area with a radius of greater than 100 nm with a DNA molecule in the center. DNA can be immobilized in the region by standard methods. For example, acrydite-modified DNA fragments can be attached to a surface modified with thiol groups and amine-modified DNA fragments can be attached to epoxy or aldehyde modified surfaces.

Typical useful polymerase enzymes include DNA polymerases with or without 3' to 5' exonuclease activities, such as for example, *E. coli* DNA polymerase I, Klenow fragment of *E. Coli* DNA polymerase I, phusion DNA polymerase, 9 N and Therminator DNA polymerase, reverse transcriptase, Taq DNA polymerase, Vent DNA polymerase (all available from New England Biolabs, Inc., Beverly, Mass.), T4 and T7 DNA polymerases, and Sequenase (all available from USB, Cleveland, Ohio). Nuclease-resistant nucleotides can be ribonucleotides or other modified nucleotides. A variety of polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant nucleotides that can be incorporated into growing DNA strands but that are resistant to digestion by exonucleases (such as the 3' to 5' exonuclease active DNA polymerases or exonuclease I and III) include alpha-phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases. Phi-29 DNA polymerase (available from New England Biolabs) provides strand displacement activity and terminal deoxynucleotide transferase provides template independent 3' terminal base addition.

Figure 8:
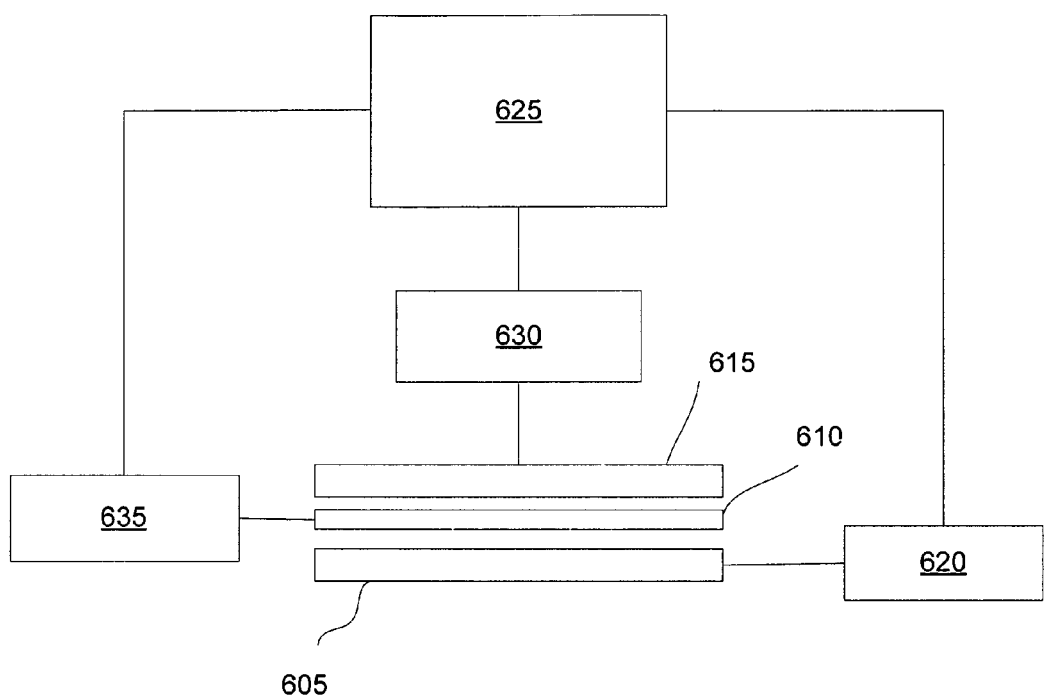
FIG. 8 provides a schematic diagram of a DNA sequencing system.

FIG. 8 provides a diagram of an exemplary DNA sequencing system. In FIG. 8, a light source 605 is placed below a reaction substrate 610 and an imager 615 is placed above the reaction substrate 610. The reaction substrate 610 consists of a waveguide and surface-attached DNA molecules to be sequenced and surface-attached PPi chelating molecules (not shown). The light source 605 is, for example, a 488 nm laser, a 514 nm laser, a 532 nm laser, and other light sources based on dyes. These light sources are commercially available. The imager 615 is, for example, a CCD (charge coupled device) camera, a cooled CCD camera, a deep cooled EMCCD (electron multiplying charge coupled device) camera or PMT (photomultiplier tube) array. Imaging devices are commercially available from, for example, Hamamatsu Photonics, Hamamatsu City, Japan. A light source control 620 controls the operation of the light source 605 and is operably connected to the computer 625. The light source control 620 is for controlling the intensity and duration of light. An acousto-optic modulator can be used for this purpose. Acousto-optic modulators are commercially available, for example, from Sintec Optronics Pte Ltd., Singapore, Malaysia. The imaging control 630 is operably coupled to the imager 615 and the computer 625. Normally the high end cameras come with their own controllers. However, there are some commercial available universal controllers for image acquisition applications, such as NI image acquisition cards (commercially available from, for example, National Instruments Corporation, Austin, Tex.). Additionally, a reagent storage and fluidic control device 635 provides reagents to the reaction region and is operably coupled to the computer 625 that directs its operation. The reagents are typically supplied in volumes in the µl to ml range. Standard devices, such as commonly used labware, plastic or glass tubes, or bottles can be used to supply reagents for DNA sequencing reactions. Reagent delivery in principle is similar to reagent delivery in HPLC (high pressure liquid chromatography) applications. Various commonly used pumps or vacuum device can be used. Typically, there are three major parts in the reagent delivery system: a) reagent storage devices, b) a reaction chamber, and c) waste container(s). A fluidic pumping system under computer control (similar to a HPLC system) is used to connect the three parts. The connection can be done by tubing, or parts mechanically fabricated by well-known methods. A mixing mechanism for solutions may also be used. Stored reagents kept separately include, four solutions of signaling nucleotides (fluorescently-labeled, each of the four nucleotides), one to four solutions for bifunctional nucleotides (nuclease resistant and 3' reversibly blocked dNTPs), an enzyme solution, a washing solution which has typically the same composition as the enzymatic reaction buffer, and a nucleotide de-blocking reagent. Other reagent storage spaces may also provided for system flexibility. Under the control of the computer program, one or more reagents can be delivered to the reaction chamber. The reagents can mixed before or after entering the chamber. Used reagents are withdrawn and disposed in a waste container. These storage devices may be stored at room temperature, or at 4° C. A wash solution containing the same buffer components as a reaction buffer can be used to clean the surface of the waveguide. To reuse the chelator, bound PPi can be removed using weak acid, such as acetic acid (having a concentration, for example, of 1 mM to 1 M). The waveguide surface can be reconditioned with the wash conditions. An additional wash solution may be needed when additional components required by the chelator need to be added back to the surface, such as metal ions ($Zn^{2+}$). Optionally, the device of FIG. 8 can be a miniaturized device, such as a microfluidic or a nanofluidic device. The computer automates the control of the delivery of reagents, monitors the results from optical measurements, and assembles sequence data from multiple reactions. Microscale fluidic devices typically have interior features for fluid flow and containment having diameters of 500 µm or less. A micrometer (µm) is $10^{-6}$ meters. Nanoscale fluidic devices typically have interior features for fluid flow and containment having diameters of 500 nm or less. A nanometer (nm) is $10^{-9}$ meters.

In various embodiments of the invention, sequencing substrates may be incorporated into a larger apparatus and/or system. In certain embodiments, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.*, 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

The electronic components of MEMS may be fabricated using integrated circuit (IC) processes (for example, CMOS (complementary metal-oxide semiconductor) and bipolar, or BICMOS processes). The components may be patterned using photolithographic and etching methods known for computer chip manufacture. The micromechanical components may be fabricated using compatible micromachining processes that selectively etch away parts of the silicon wafer or add new structural layers to form the mechanical and/or electromechanical components.

Basic techniques in chip manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

In some embodiments of the invention, substrates may be connected to various fluid filled compartments, such as microfluidic channels, nanochannels, and or microchannels. These and other components of the apparatus may be formed as a single unit, for example in the form of a chip, such as semiconductor chips and or microcapillary or microfluidic chips. Alternatively, the substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz. These materials are especially useful for plasmonic waveguide devices which do not require a substrate that is transparent. For zero mode waveguide devices, the substrate itself or a layer of the substrate typically is transparent, and a substance such as a glass or silicon nitride is useful as the substrate material or as a layer on a substrate in contact with the patterned metal layer.

EXAMPLES

Synthesis and Attachment of Pyrophosphate Chelators to a Substrate Surface

Figure 9:
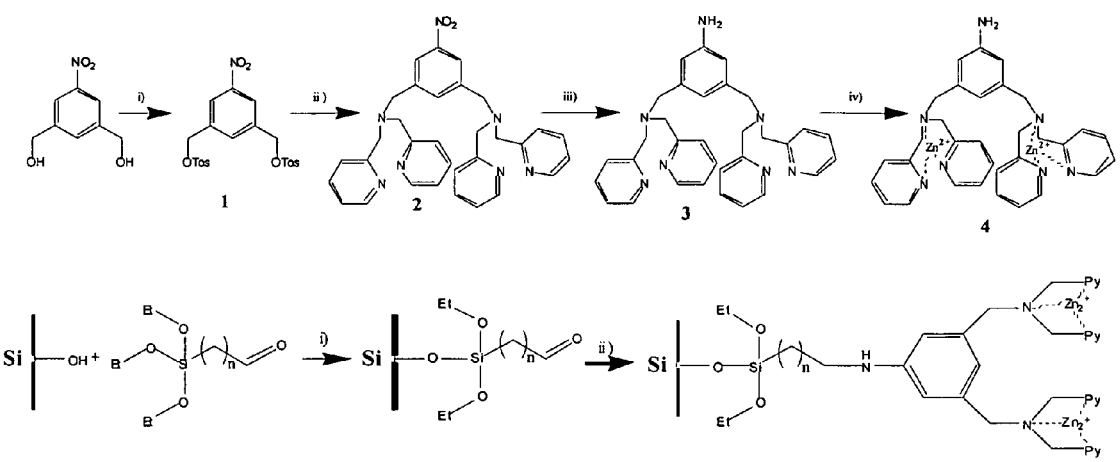
FIG. 9 shows an exemplary synthesis scheme for a surface-attached chelating molecule.

The pyrophosphate chelator was designed with three main components: a binding site, a linker, and a handle. The binding site was designed to bind PPi selectively, the linker between the binding site and chelator provides steric flexibility to the overall molecule if needed and the handle ensures that the chelator can be attached to a surface. The selected PPi chelator has demonstrated high binding capability to PPi. Referring to FIG. 9, the starting material for the synthesis of the surface-attachable pyrophosphate chelator was 5-nitro-1,3-bishydroxymethylbenzene, whose hydroxyl groups were tosylated to accelerate the substitution reaction in the next synthesis reaction. The tosylate groups were replaced by dipyridinylamine. The nitro group was reduced efficiently to an amine group by catalytic hydrogenation using Pd C and $H_2$. The zinc nitrate ($Zn(NO_3)_2$) was added afterwards to yield the final functional pyrophosphate chelator.

The synthesized pyrophosphate chelator was immobilized on a substrate surface that had been silanated. An aldehyde group was used to functionalize the silicon surface through derivatization of the silicon surface with 4-(triethoxysilyl) butyraldehyde. Reductive amination with sodium triacetoxyborohydride was used to covalently attach the pyrophosphate chelator to the derivatized substrate surface. Immobilization of the pyrophosphate chelator was confirmed: the substrate surface was characterized by ellipsometry, atomic force microscope (AFM) and TOF-SIMS (time-of-flight secondary ion mass spectroscopy). Monolayer thicknesses and sample topography were consistent with step-by-step surface modification of silicon substrate surface. Ellipsometry and AFM data indicated a thickness of about 35 Å for the pyrophosphate chelator and its linker, consistent with the expected value. TOF-SIMS measurements of modified substrate surfaces yielded the expected mass of the immobilized pyrophosphate chelator while the pyrophosphate chelator was not detected on several types of control samples.

Binding kinetics: The newly synthesized immobilizable pyrophosphate chelator was subjected to selective binding studies using a coumarin-based fluorescent dye, (6,7-dihydroxy-2-oxo-2H-chromen-4-yl)methanesulfonate, and a colorimetric dye, pyrocatechol violet (PV). In case of fluorescent dye, binding to the chelator caused quenching of its fluorescence. As more chelator was added, fluorescence intensity decreases showing dose response as expected that reached a plateau near 10 μM. The dose response curve was used to estimate the binding constant for this fluorescent dye at $1.7 \times 10^6$ $M^{-1}$. This binding constant was similar to what was reported for a similar pyrophosphate chelator. When the colorimetric dye was used, the binding to pyrophosphate chelator caused a detectable color change from blue (free dye, $\lambda_{max}$ 444 nm) to yellow (complex, $\lambda_{max}$ 624 nm). The peak absorption change from blue (free dye, $\lambda_{max}$ 444 nm) to yellow ($\lambda_{max}$ 624 nm) indicated formation of chelator-dye complex. This color change was visible to naked eye.

To study selectivity of the immobilizable pyrophosphate chelator, the binding of PPi to the chelator was compared to the binding of phosphate (Pi) and dATP. Both fluorescence and absorption data indicated that the chelator showed selectivity for PPi over Pi and dATP. A competitive displacement assay of the immobilizable chelator with PPi, dATP, and Pi was performed. 1:1 mixtures of chelator and fluorescent dye were treated with various concentrations of binders. Fluorescence was monitored at 480 nm with excitation at 347 nm. Other dNTPs were also studied in competitive displacement assays. The immobilizable chelator was found to bind PPi preferentially over other dNTPs, similar to the results for dATP.

The invention claimed is:

1. A device comprising:
a substrate, included in a waveguide, wherein the substrate has a surface that comprises both: (a) a plurality of attachment sites for nucleic acid molecules to be sequenced, and (b) a plurality of attached molecules capable of chelating a pyrophosphate ion,
an optical system comprising a light source, a light source control, and an image detector,
an electronics system operably coupling a computer to the optical system,
a function layer having a first index of refraction, and
a layer, included in the waveguide and directly contacting the function layer, having a second index of refraction greater than the first index of refraction,
wherein the computer is capable of receiving, storing, and processing data from the electronics system in order to assemble the sequence of a nucleic acid molecule to be sequenced,
wherein the light source is positioned so light from the light source is directed: (a)(i) into and orthogonal to a first side of the waveguide, and (a)(ii) parallel to a second side of the waveguide;
wherein the second side of the waveguide includes the surface of the substrate.

2. The device of claim 1 comprising:
an inlet oriented and proportioned to fluidly couple with fluid from a fluid delivery system;
wherein the substrate is a planar waveguide and the surface fluidly couples to the inlet to receive and directly contact the fluid.

3. The device of claim 2 wherein the planar waveguide comprises $SiO_2$.

4. The device of claim 2 also comprising the fluid delivery system, wherein the fluid delivery system is comprised of a plurality or reservoirs capable of containing a plurality of solutions and a plurality of outlets from the plurality of reservoirs capable of delivering fluids to the surface of the substrate.

5. The device of claim 2 wherein the electronics system is capable of causing a solution from a reservoir to be supplied to the surface of the substrate and wherein the computer is capable of directing the electronics system to supply a solution from a reservoir to the surface of the substrate.

6. A device comprising:
a substrate including a zero mode waveguide having a surface wherein the surface comprises a plurality of attachment sites for nucleic acid molecules to be sequenced and a plurality of attached molecules capable of chelating a pyrophosphate ion and wherein the surface comprises a patterned metal layer wherein the patterned metal layer has a thickness of between 1 nm and 100 nm,
an optical system comprising a light source, a light source control, and an image detector,
an electronics system operably coupling a computer to the optical system, and the computer capable of receiving, storing, and processing data from the electronics system in order to assemble the sequence of a nucleic acid molecule to be sequenced;

wherein the patterned metal layer comprises holes in the metal layer, the holes have diameters that are less than a wavelength of light from the light source, and the wavelength of light is capable of exciting a molecule for which an emission is to be detected by the image detector.

7. The device of claim 6 wherein the attachment sites for nucleic acid molecules to be sequenced are located within the holes.

8. The device of claim 7 wherein the metal layer comprises at least one of is comprised of silver, gold, and copper.

9. The device of claim 7 also comprising a fluid delivery system, wherein the fluid delivery system is comprised of a plurality or reservoirs capable of containing a plurality of solutions and a plurality of outlets from plurality of reservoirs capable of delivering fluids to the surface of the substrate.

10. The device of claim 9 wherein the electronics system is capable of causing a solution from a reservoir to be supplied to the surface of the substrate and wherein the computer is capable of directing the electronics system to supply a solution from a reservoir to the surface of the substrate.

11. A device comprising:
a substrate that is capable of functioning as a plasmonic waveguide having a surface wherein the surface comprises a plurality of attachment sites for nucleic acid molecules to be sequenced and a plurality of attached molecules capable of chelating a pyrophosphate ion and wherein the surface comprises a patterned metal layer having holes and the attachment sites for nucleic acid molecules and the plurality of attached molecules capable of chelating a pyrophosphate ion are located within the holes, an optical system comprising a light source, a light source control, and an image detector, an electronics system operably coupling a computer to the optical system, and the computer capable of receiving, storing, and processing data from the electronics system in order to assemble the sequence of a nucleic acid molecule to be sequenced.

12. The device of claim 11 wherein the holes in the patterned metal layer have a dimension that is larger than a wavelength of light from the light source wherein the wavelength of light is capable of exciting a molecule for which an emission is to be detected by the image detector.

13. The device of claim 12 wherein the metal layer comprises at least one of silver, gold, and copper.

14. The device of claim 12 also comprising a fluid delivery system, wherein the fluid delivery system is comprised of a plurality or reservoirs capable of containing a plurality of solutions and a plurality of outlets from the plurality of reservoirs capable of delivering fluids to the surface of the substrate.

15. The device of claim 14 wherein the electronics system is capable of causing a solution from a reservoir to be supplied to the surface of the substrate and wherein the computer is capable of directing the electronics system to supply a solution from a reservoir to the surface of the substrate.

16. The device of claim 2 wherein the molecules capable of chelating a pyrophosphate ion comprise a detectable label.

17. The device of claim 7 wherein the molecules capable of chelating a pyrophosphate ion comprise a detectable label.

18. The device of claim 12 wherein the molecules capable of chelating a pyrophosphate ion comprise a detectable label.

19. The device of claim 2, wherein the function layer includes the surface of the substrate.

20. The device of claim 19, wherein the plurality of attached molecules capable of chelating a pyrophosphate ion each include a linker.

* * * * *